(12) United States Patent
Tejani

(10) Patent No.: US 9,302,075 B2
(45) Date of Patent: Apr. 5, 2016

(54) CATHETER RETENTION DEVICE

(71) Applicant: Furqan Tejani, Yonkers, NY (US)

(72) Inventor: Furqan Tejani, Yonkers, NY (US)

(*) Notice: Subject to any disclaimer, the term of this patent is extended or adjusted under 35 U.S.C. 154(b) by 137 days.

(21) Appl. No.: 13/871,945

(22) Filed: Apr. 26, 2013

(65) Prior Publication Data

US 2014/0324024 A1    Oct. 30, 2014

(51) Int. Cl.
*A61M 5/178* (2006.01)
*A61M 5/32* (2006.01)
*A61M 25/02* (2006.01)

(52) U.S. Cl.
CPC .......... *A61M 25/02* (2013.01); *A61M 2025/024* (2013.01); *A61M 2025/028* (2013.01)

(58) Field of Classification Search
CPC .......... A61M 25/02; A61M 2025/024; A61M 2025/028
USPC ................ 604/174, 178–180, 164.04, 164.08
See application file for complete search history.

(56) References Cited

U.S. PATENT DOCUMENTS 5,069,206 A * 12/1991 Crosbie .................... 128/207.17
5,755,225 A * 5/1998 Hutson .................... 128/207.18

* cited by examiner

*Primary Examiner* — Rebecca E Eisenberg
(74) *Attorney, Agent, or Firm* — Schwabe, Williamson & Wyatt, P.C.

(57) ABSTRACT

Embodiments provide catheter retention devices such as catheter clips that may be used to stabilize a vascular access catheter during a procedure, particularly a radial access procedure. The catheter clips may include a frame that includes a first frame member portion, a second frame member portion hingeably coupled to the first frame member portion, the first and second frame member portions defining a first aperture therebetween, and a base member extending from the second frame member; and an inner gripping membrane that includes a first inner gripping membrane portion coupled to the first frame member portion and a second inner gripping portion coupled to the second frame member portion, wherein the first and second inner gripping portions define a second aperture within the first aperture.

20 Claims, 9 Drawing Sheets

CATHETER RETENTION DEVICE

TECHNICAL FIELD

Embodiments relate to methods and devices for stabilizing catheters during percutaneous vascular and cardiac procedures, such as diagnostics and interventions, and particularly to methods and devices for stabilizing catheters during radial, brachial, and/or axillary access to the vasculature.

BACKGROUND

Radial artery access for percutaneous vascular and cardiac interventions and diagnostics has been shown to reduce complications when compared to the standard femoral artery approach. For example, interventions accomplished via the radial artery carry a lower risk of bleeding complications and a higher rate of early ambulation. However, such an approach is complicated and requires a number of steps in order to traverse multiple vascular tortuosities in order to carry out the interventions or diagnostics.

For example, in many cases, radial artery access entails traversing two or three acute bends within the vasculature before reaching a final destination. Often, these acute bends may be separated by relatively long distances, which can cause the catheter to shift or back out of position once it has been placed if continuous torque on the catheter is not maintained. When a single operator is performing the procedure, it may be necessary to try to stabilize the catheter by placing a towel or other object across the external portion of the catheter in order to hold it in position. Such techniques are unreliable, and may allow the catheter to move after it has been placed. Such post-placement shifting of the catheter may cause problems during procedures, and may increase the length of the procedure, and/or may involve increased trauma for the patient as the catheter is repositioned.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

DETAILED DESCRIPTION OF DISCLOSED EMBODIMENTS

Figure 1:
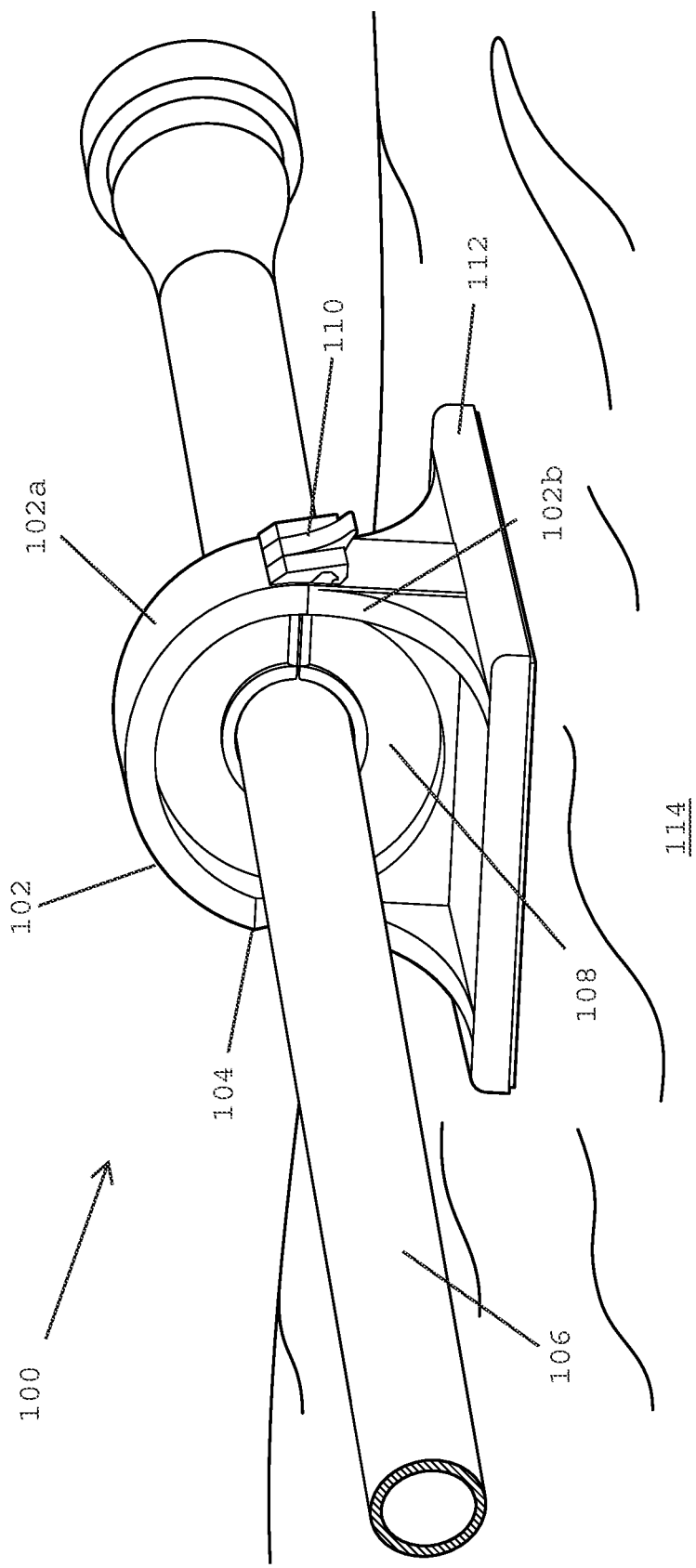
FIG. 1 illustrates an embodiment of a catheter clip securing a catheter in position.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact. However, "coupled" may also mean that two or more elements are not in direct contact with each other, but yet still cooperate or interact with each other.

For the purposes of the description, a phrase in the form "NB" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

Embodiments herein provide catheter retention devices that may be used to retain a catheter in a desired position once it has been positioned within the vasculature. In various embodiments, the catheter retention device may include a catheter clip that may be selectively opened and closed about a catheter without crimping or otherwise impinging upon the catheter, and yet may retain the catheter in a proximal-distal direction and/or a rotational direction once the catheter has been placed within the vasculature.

In some embodiments, the catheter clip may have a rigid or semi-rigid frame member, such as a rubber, silicone, plastic, or metal frame member, that may be configured to support an inner gripping membrane that is adapted to atraumatically grip and stabilize the catheter once it has been positioned in the vasculature of a subject. In various embodiments, the frame member may include two frame portions, such as an upper portion and a lower portion, joined on one side by a hinge member, and the two frame portions may be adapted to selectively couple and uncouple on the opposite side, thereby closing the inner gripping membrane about the outer circumference of the catheter. Some embodiments of the frame member may be a single, unitary piece, whereas other embodiments may include two pieces joined by the hinge member. The frame member also may include one or more closure elements to secure the clip in a closed position about the catheter, and in some embodiments, the closure element may be adapted to generate an audible or tactile indication of closure.

Various embodiments of the catheter clip may have an inner gripping membrane that is adapted to grip the catheter with a predetermined gripping force. In some embodiments, the predetermined gripping force may be selected to resist a predetermined torque. In some embodiments, the inner gripping membrane may be a thin elastomeric membrane, such as a thin membrane formed from rubber, latex, silicone, or elastomeric plastic. In other embodiments, the membrane may be thicker, and/or may include notches, folds, ribs, or other elements designed to produce a desired amount of torque resistance without crimping or otherwise impinging upon the catheter during use.

In some embodiments, the inner gripping membrane may grip the catheter with sufficient force to impede accidental rotational and/or proximal/distal movement of the catheter through the catheter clip, but may still allow an operator to advance, retract, and/or rotate the catheter within the catheter clip with the application of a sufficient force. In other embodiments, it may be necessary to uncouple the two frame portions from one another in order to rotate, retract, or advance the catheter.

In some embodiments, the frame member also may include a base portion adapted to couple to a drape or dressing, a portion of the patient's skin, or another convenient surface, for instance via a non-slip or adhesive element. In various embodiments, the coupling power of the non-slip or adhesive element may be sufficiently strong to retain the position and orientation of the catheter clip even under torque or tension from the catheter. Although an adhesive member is illustrated herein, one of skill in the art will appreciate that other means for securing the catheter clip in position may be provided, such as a hook-and-loop type fastener, a snap, or a suction cup, depending on the surface to which the user wishes to attach the catheter clip.

In some embodiments, the catheter clip may be a single-use item, and in other embodiments the catheter clip may be configured to be sterilized and reused. In some embodiments, the catheter clip may be designed to be opened and closed a number of times without breaking, for example at least 25-30 times. Some embodiments of the catheter clip may be designed to accommodate a range of catheter sizes, such as 3 French to 7 French, or 4 French to 6 French, whereas other embodiments of the catheter clip may be designed to accommodate a particular size of catheter, such as 4 French, 4.5 French, 5 French, 5.5 French, or 6 French.

FIG. 1 illustrates an embodiment of a catheter clip securing a catheter in position. In the illustrated embodiment, catheter clip 100 includes a frame member 102 having an upper portion 102a and a lower portion 102b. In various embodiments, upper portion 102a and lower portion 102b may be hingeably connected at hinge portion 104. In some embodiments, upper portion 102a and lower portion 102b may be separate pieces that are coupled at hinge portion 104. However, in the illustrated embodiment, upper portion 102a, lower portion 102b, and hinge portion 104 are all part of a single-piece frame member 102.

Although hinge portion 104 is located on the side of catheter clip 100 in the illustrated embodiment, one of skill in the art will appreciate that in alternate embodiments the hinge may be positioned at the bottom of frame 102, with the opening at the top of catheter clip 100, or it may be positioned at an angle, for example with the opening on the diagonal. One of skill in the art also will appreciate that although upper portion 102a and lower portion 102b are illustrated as being approximately equal in size, they may be asymmetrically sized in other embodiments. Likewise, although they are shown as having a circular profile with a round aperture within, they may be ovoid, square, triangular, hexagonal, or any other shape, be it regular or irregular.

Frame member 102 may be made from any material having sufficient strength and rigidity to support inner gripping membrane 108 and to secure catheter 106 in position. For instance, in some embodiments, frame member 102 may be made from plastic or a polymer, such as vacuum-formed, co-molded, injection-molded, or extruded plastic, polyethylene, or polypropylene. In other embodiments, frame member 102 may be made from rubber, latex, silicone, metal, or any other suitable material having the desired properties. Hinge portion 104 may be any kind of hinge that permits upper portion 102a to pivot relative to lower portion 102b, and may be made from any suitable material, such as polyethylene, polypropylene, plastic, rubber, latex, silicone, or metal.

In embodiments wherein frame member 102 is a single, unitary piece, hinge 104 may be a living hinge. Such a living hinge is a thin and flexible flexure bearing hinge made from the same material as the two rigid (or semi-rigid) pieces it connects, rather than a separate, flexible member. In various embodiments, a living hinge may be thinned or cut to allow the rigid (or semi-rigid) pieces to bend along the line of the hinge. The minimal friction and very little wear in such a hinge makes it durable, and the low cost and ease of manufacturing makes it suited to disposable devices. In various embodiments, a closure mechanism 110 may be provided opposite hinge member 104 that may secure catheter clip 100 in a closed position during use. Closure mechanism 110 may be any type of selectably engageable closure mechanism, and in some embodiments, may produce audible or tactile feedback to the user when engaged.

As described above and illustrated in FIG. 1, frame member 102 is adapted to support inner gripping membrane 108. In some embodiments, inner gripping membrane may be coupled to and/or extend inwardly from frame member 102, and may be adapted to grip catheter 106 securely without crimping or otherwise impinging upon catheter 106. In various embodiments, inner gripping membrane 108 may be formed from any suitable material having sufficient gripping power and elasticity to substantially immobilize catheter 106 when frame 102 is closed thereabout. In some embodiments, for example, inner gripping membrane 108 may be formed from latex, rubber, silicone, or a polymer, such as polyethylene or polypropylene. In some embodiments, inner gripping membrane 108 may be coupled to frame 102 using any conventional coupling mechanism, such as glue, adhesive, or a physical interlocking mechanism such as a tongue-in-groove structure. In other embodiments, inner gripping membrane may be continuous with frame 102, and may be made from the same material, such as latex, rubber, silicone, polystyrene, or polyethylene. In some embodiments, the gripping power of inner gripping membrane 108 may be adjusted to suit a particular application by adjusting the thickness, shape, or contour of the material it is made from. Additionally, the inner aperture of inner gripping membrane may be sized to fit a range of catheters, or it may be sized to fit a particular size of catheter, such as 4 French, 4.5 French, 5 French, 5.5 French, or 6 French.

In various embodiments, frame 102 also may include a base member 112 that may be configured to couple to a substrate, such as drape 114. In some embodiments, base member 112 may be secured to drape 114 (or another substrate or surface) via an adhesive patch, a hook-and-loop mechanism, a magnet, a suction cup, or any other attachment mechanism suitable for the surface to which it will be coupled. In other embodiments, base member 112 may simply be weighted, or may be provided with a non-slip lower surface, such as a rubberized surface, that may retain catheter clip 100 in positing during use.

Figure 2:
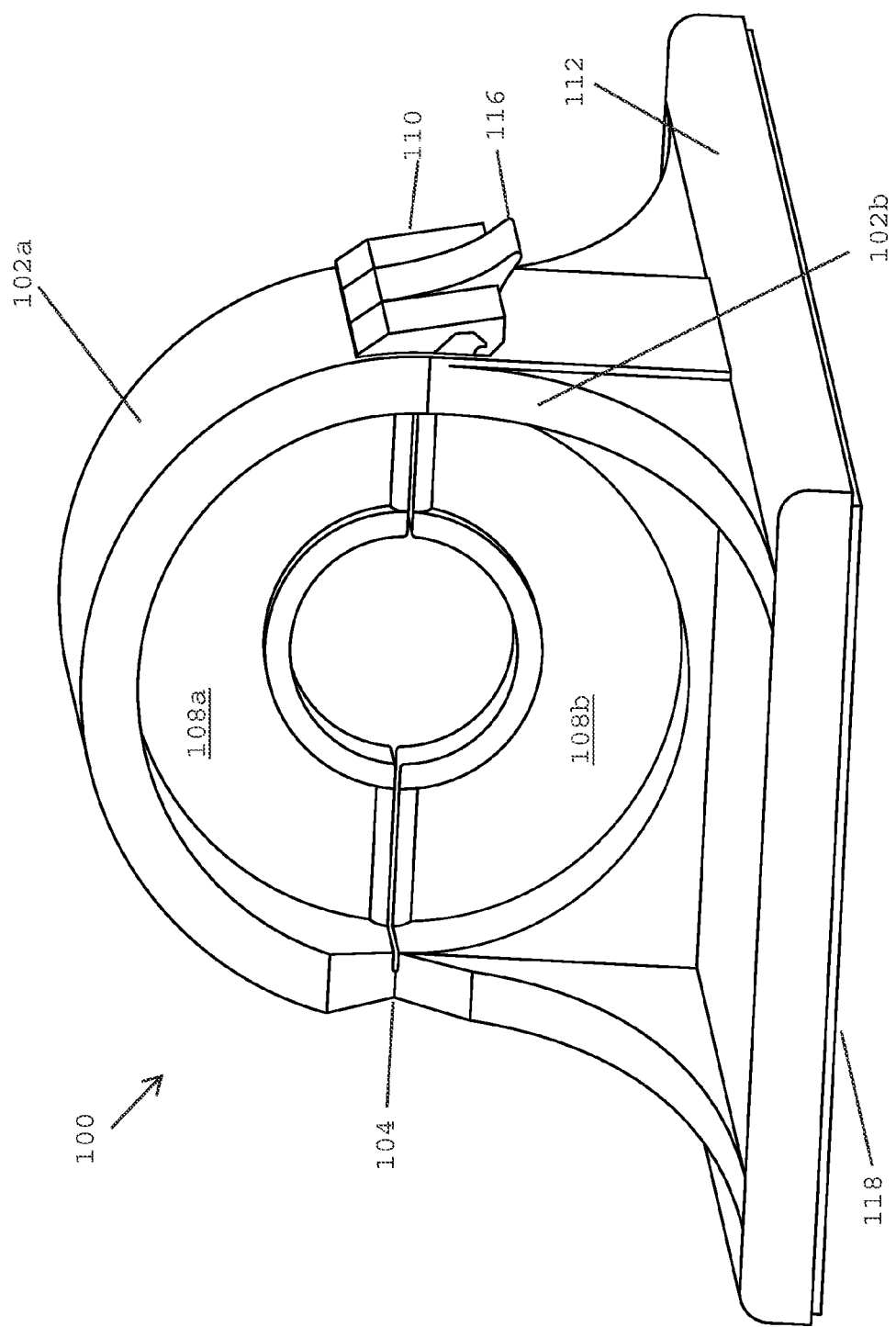
FIG. 2 illustrates a close-up perspective view of the catheter clip of FIG. 1.

FIG. 2 illustrates a close-up perspective view of the catheter clip of FIG. 1. As illustrated, in various embodiments, the inner gripping member 108 of catheter clip 100 may include two portions 108a, 108b that correspond to the two portions of the frame member 102a, 102b. In addition, hinge member 104 may include tapers or cutouts that facilitate a wide angle of operation of the hinge member 104.

Also shown in this view is closure mechanism 110, which may include a thumb tab 116 to help facilitate opening and closing of the closure mechanism 110. An adhesive element 118 or other coupling element may be located on a bottom surface of base member 112. Although an adhesive member is illustrated, on of skill in the art will appreciate that other coupling mechanisms or non-slip elements may be substituted.

Figure 3:
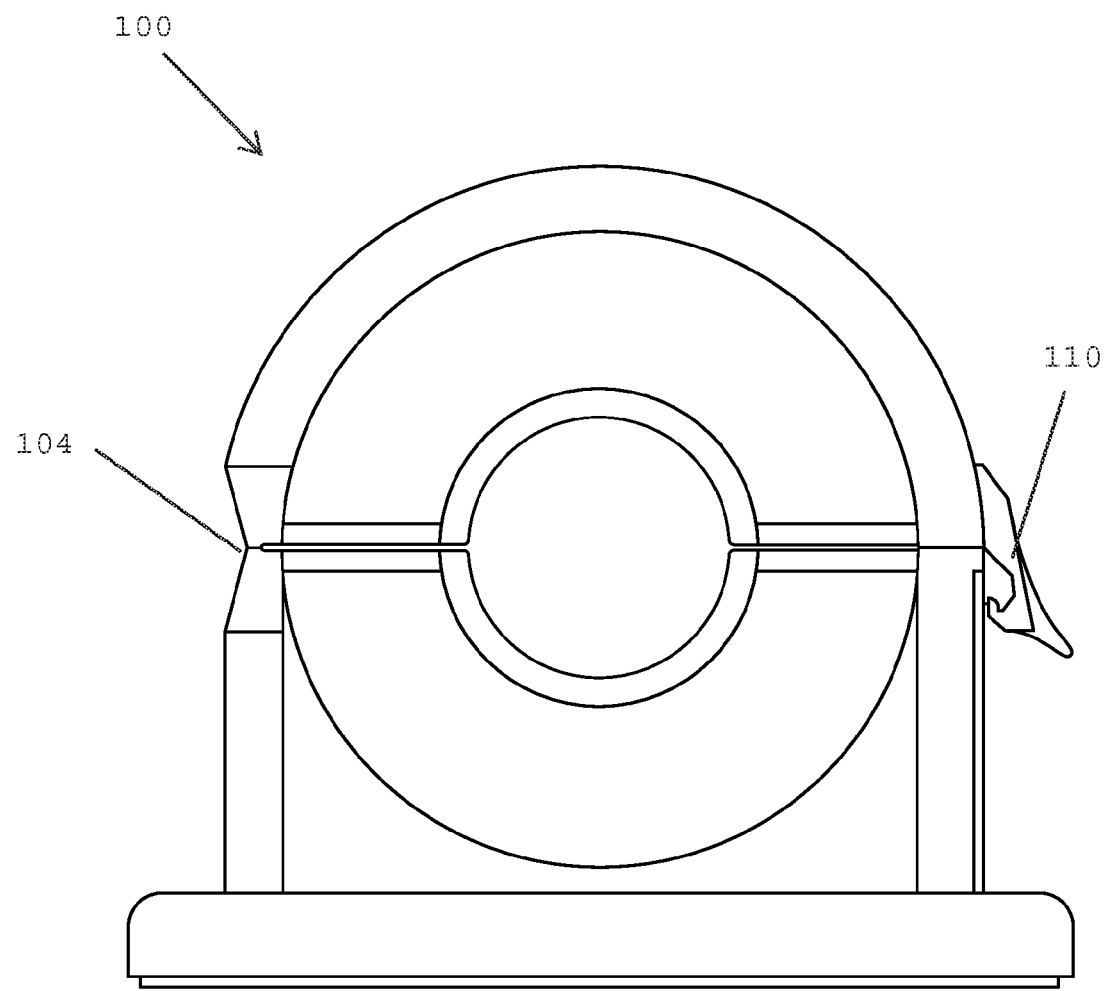
FIG. 3 illustrates a side view of the catheter clip of FIG. 1 in a closed position.
Figure 4:
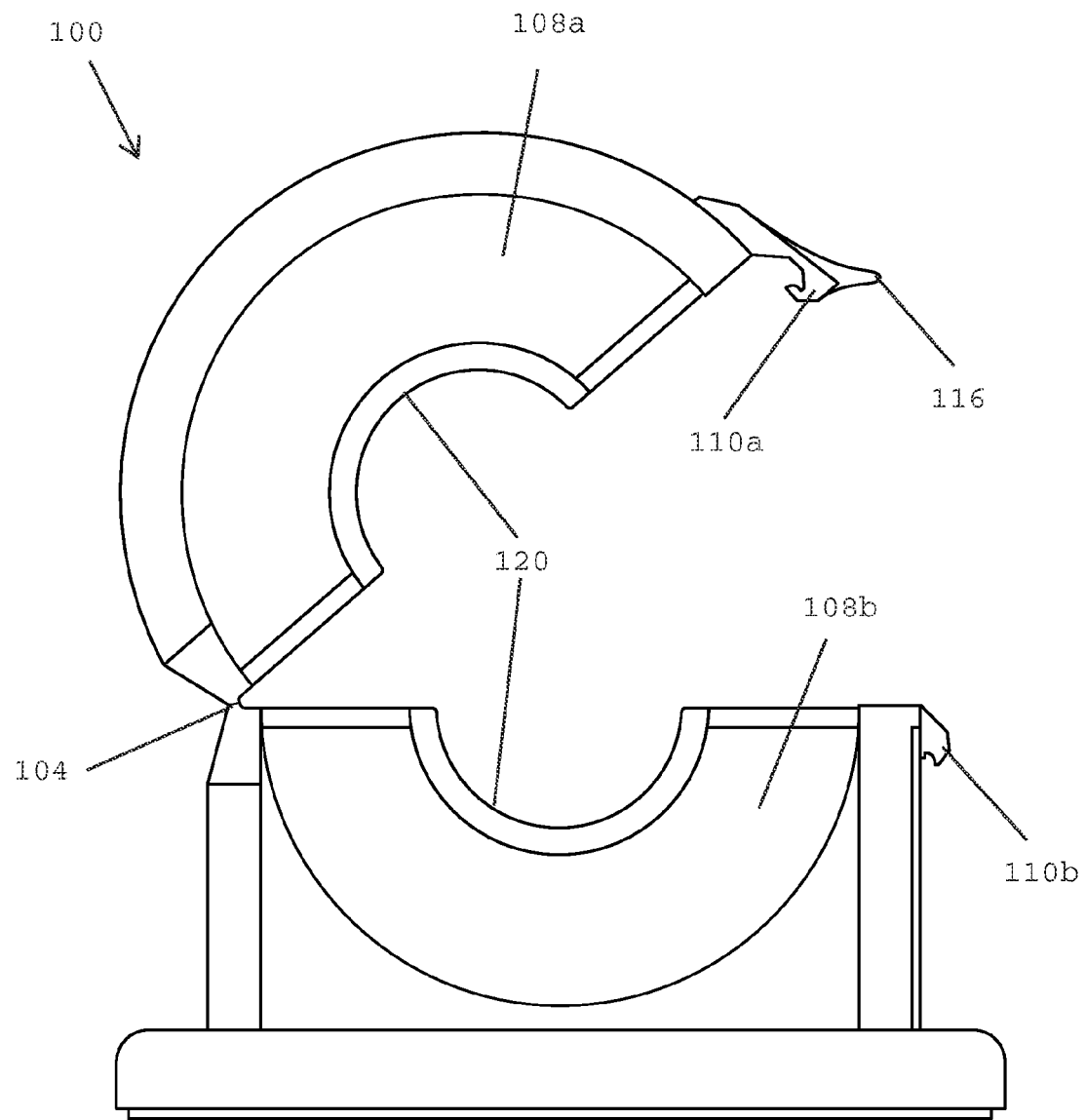
FIG. 4 illustrates a side view of the catheter clip of FIG. 1 in an open position.

FIGS. 3 and 4 illustrate a side view of the catheter clip of FIG. 1 in a closed position (FIG. 3) and in an open position (FIG. 4). In the illustrated embodiment, catheter clip 100 includes a hinge member 104 opposite the closure mechanism 110, and in some embodiments, the closure mechanism 110 may include a pair of interlocking hook elements 110a, 110b and a thumb tab 116. One of skill in the art will appreciate that although hook elements are illustrated, many closure mechanisms are known in the art, and any other closure mechanism that functions to selectably retain the clip in a closed position may be substituted. Alternately, the catheter clip may not include a closure mechanism at all, but instead may be biased into a closed position.

In some embodiments, inner gripping membrane 108a, 108b may include a reinforcing ring 120, which may be a thicker or stiffer portion of the inner gripping membrane 108. In some embodiments, reinforcing ring 120 may provide a greater grip on the catheter (not shown), for instance a greater ability to resist longitudinal or rotational movements of the catheter when the catheter clip 100 is closed thereabout.

Figure 5:
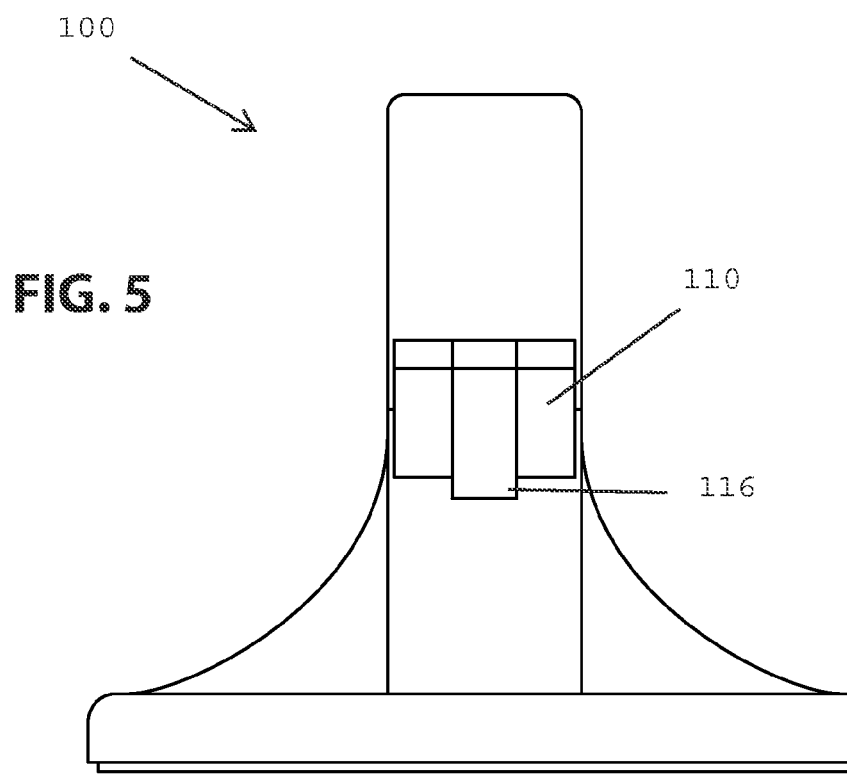
FIG. 5 illustrates a front view of the catheter clip of FIG. 1, and illustrates one embodiment of a closure mechanism.
Figure 6:
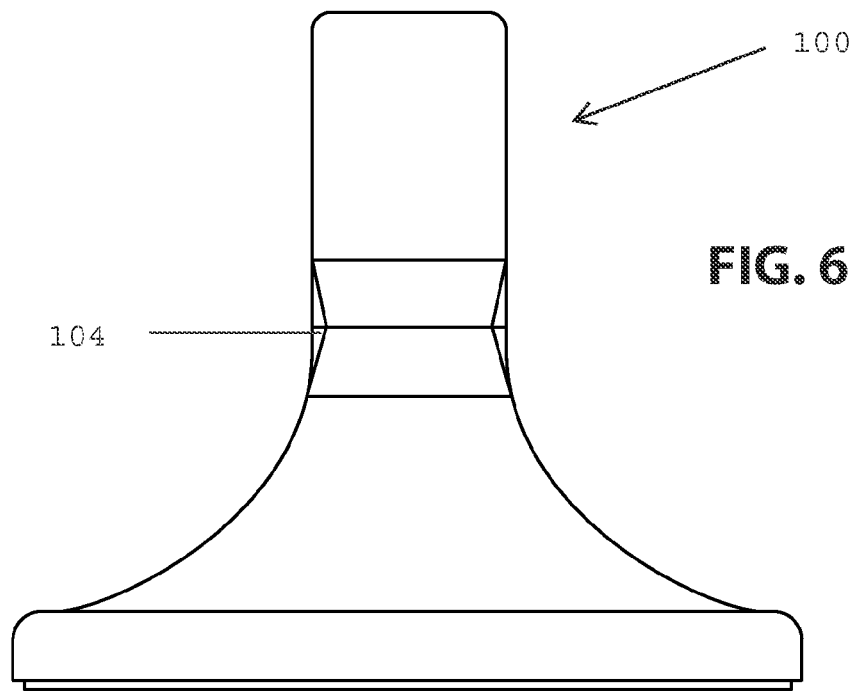
FIG. 6 illustrates a rear view of the catheter clip of FIG. 1, and illustrates one embodiment of a hinge mechanism.

FIG. 5 illustrates a front view of the catheter clip 100 of FIG. 1, and shows one embodiment of a closure mechanism 110, and FIG. 6 illustrates a rear view of the catheter clip 100 of FIG. 1, and shows one embodiment of a hinge mechanism 104. In some embodiments, closure mechanism 110 may include a thumb tab 116 or other mechanism to facilitate opening and closing of the catheter clip. In some embodiments, thumb tab 116 may project down and/or away from closure mechanism 116 in order to provide leverage to a user.

Figure 7A:
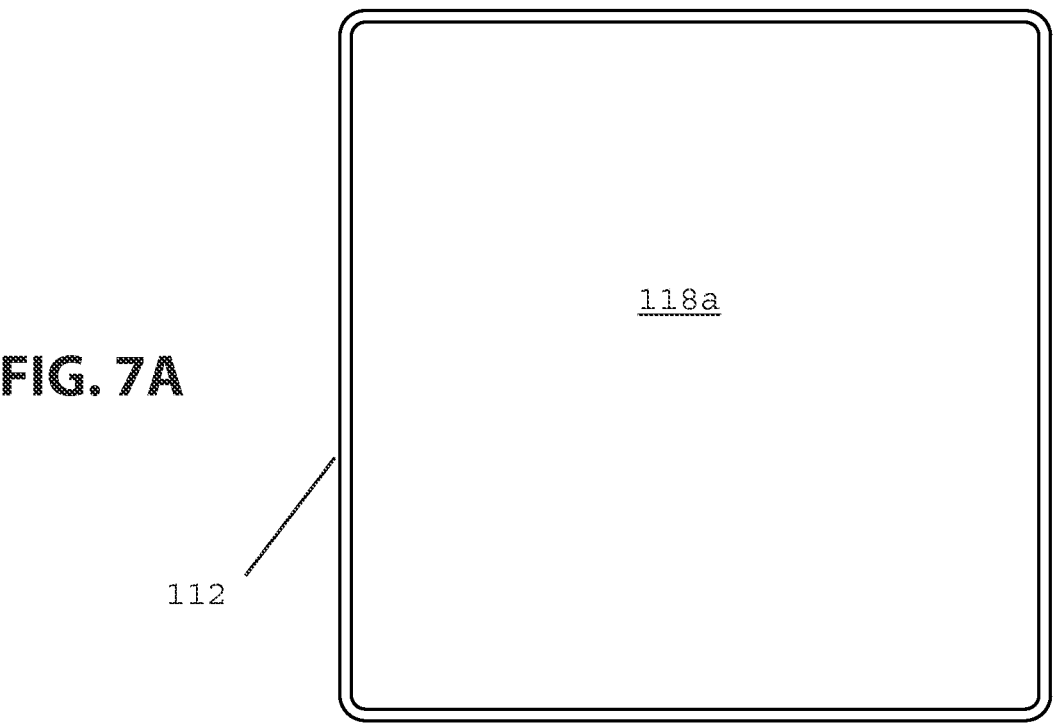
FIGS. 7A and 7B illustrate a bottom view of an embodiment of a catheter clip, showing an adhesive element with a peelable cover in place (FIG. 7A) and partially removed to expose the adhesive (FIG. 7B)
Figure 7B:
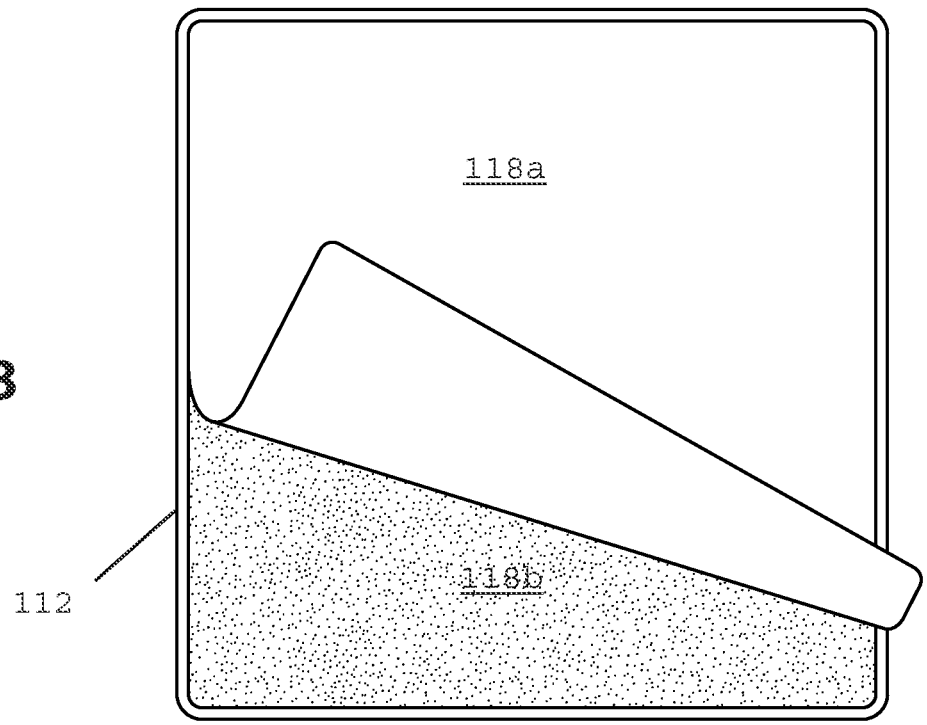

FIGS. 7A and 7B illustrate a bottom view of the base member 112 of an embodiment of a catheter clip 100, showing an adhesive element 118b with a peelable cover 118a in place (FIG. 7A), and partially removed to expose the adhesive element 118b (FIG. 7B). In use, a user may peel the peelable cover 118a to expose the adhesive element 118b before affixing the base 112 to a drape or other substrate.

Figure 8:
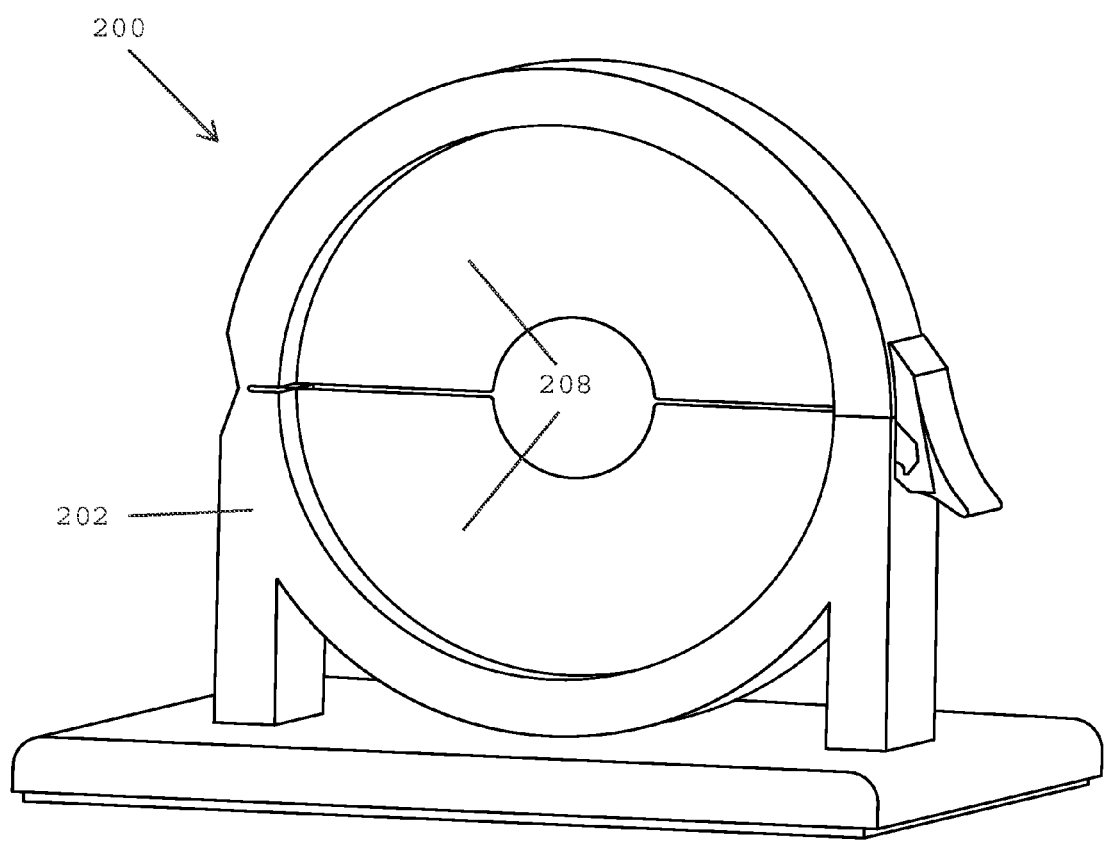
FIG. 8 illustrates a lightweight embodiment of a catheter clip.

Although a particular embodiment is illustrated in FIGS. 1-7, one of skill in the art will appreciate that the overall look and shape of the catheter clip may be modified in certain regards to suit various uses. For example, FIG. 8 illustrates a lightweight embodiment of a catheter clip 200 that is designed to be thin, light, and inexpensive. This embodiment may be of use, for example, when the catheter is thin and light or requires only light stabilization, such as when the catheter does not exert as much torque or longitudinal force once it has been placed. In this embodiment, frame member 202 may be thinner and lighter than in other embodiments, and inner gripping membrane 208 may be a thin layer of latex, silicone, rubber, or other elastomeric material with no reinforcing elements. Because this embodiment is less bulky and uses less material in the frame 202 and inner gripping membrane 208, it may be less expensive to manufacture. Such embodiments may be particularly suited to single-use catheter clips, as less material is wasted when the catheter clip is disposed of or recycled.

Figure 9:
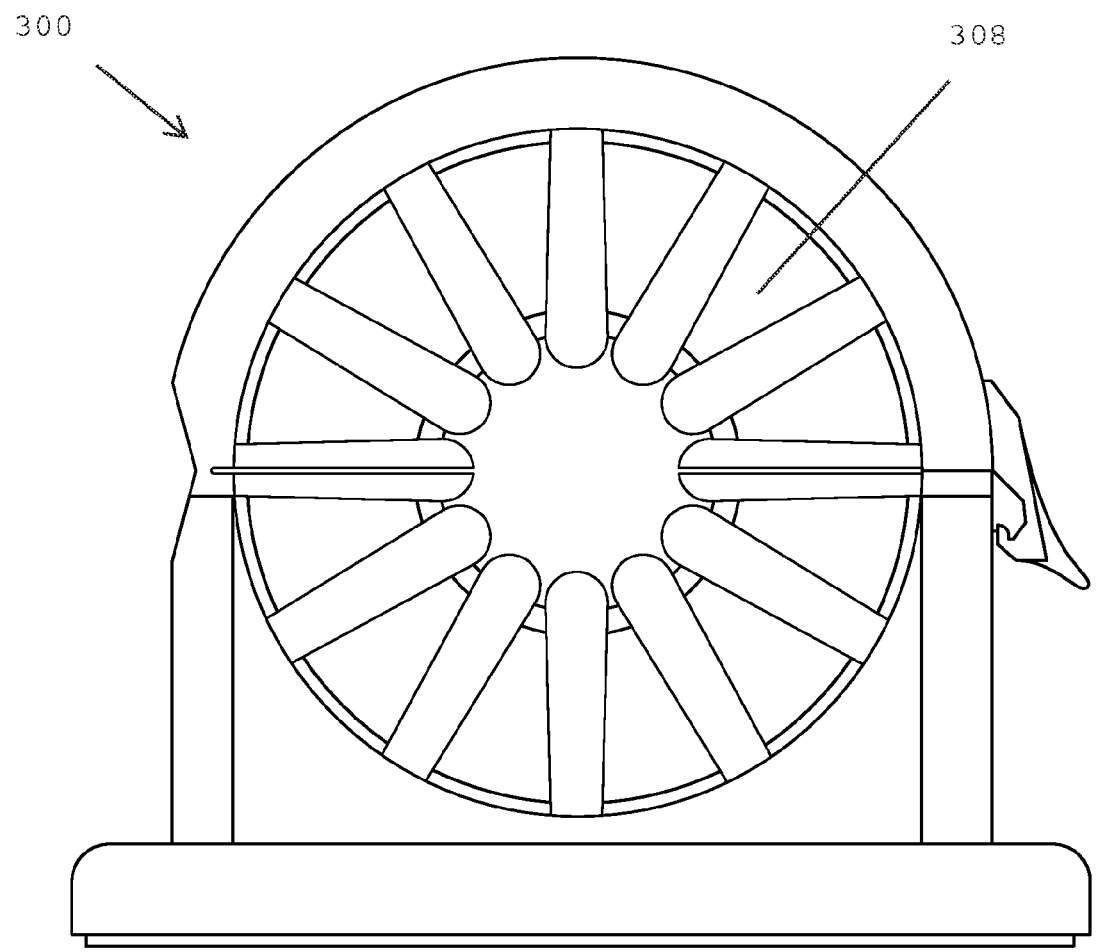
FIG. 9 illustrates a heavy duty embodiment of a catheter clip in a closed position.
Figure 10:
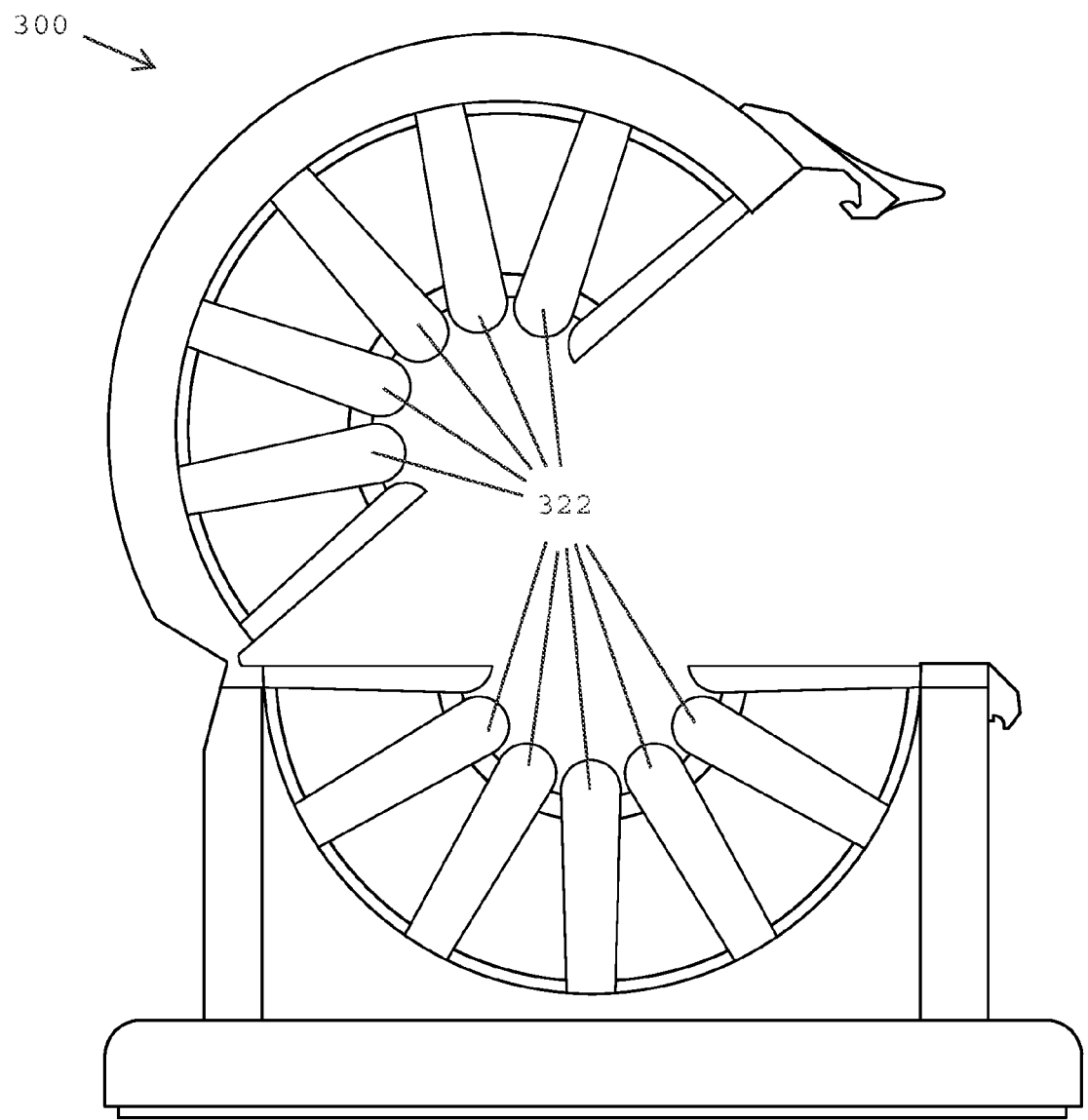
FIG. 10 illustrates the catheter clip of FIG. 9 in and open position; all in accordance with various embodiments.

FIGS. 9 and 10 illustrate a heavy duty embodiment of a catheter clip 300 in a closed position (FIG. 9) and in an open position (FIG. 10). This embodiment may be particularly useful when the catheter requires heavier stabilization, such as when the catheter exerts more torque or longitudinal force once it has been placed. In this embodiment, inner gripping membrane 308 may include a plurality of reinforcing ribs 322 that may allow the catheter clip 300 to grip the catheter more tightly. Although a particular configuration of reinforcing ribs 322 is illustrated, one of skill in the art will appreciate that more or fewer reinforcing ribs 322 may be included in other embodiments, or they may be combined with a reinforcing ring (not shown) or other stabilization element.

As described above, the disclosed catheter clips are particularly useful for stabilizing catheters during small vessel access procedures, for example radial and brachial access procedures such as for coronary, neurological, or peripheral procedures. Providing access from the arm instead of the femoral artery has advantages in enabling patients to be discharged and mobile with only a bandage, and often no closure devices are necessary. In contrast, femoral access has higher costs associated with patient management, as a closure device is often necessary, and mobility of the patient may be limited, which may significantly delay patient discharge and thereby may reduce the frequency and the number of patients that may be treated.

In one example of a procedure using radial access for cardiac catheterization or a left ventricular procedure, a guidewire may be inserted into the radial artery using but not limited to a single wall or a double wall stick technique. In one specific, non-limiting example, a catheter for use in such a procedure may have an internal diameter of about 5 French and an outer diameter of about 6 French, and also may have a lubricious coating on at least part of its distal length. The catheter may be inserted with or without a sheath and advanced over a guidewire. In some embodiments, contrast dye may be infused through the sheath, or the contrast dye may be infused directly through the catheter to assist with obtaining an anatomic roadmap. The catheter may then be advanced into the aorta, to image the coronary vasculature and left ventricular function. In various embodiments, the catheter then may be guided to the coronary ostium of the left and right coronary arteries and across the aortic valve, after which the catheter may be passed into the left ventricular chamber.

Once the catheter has been placed either in the coronary ostium or the left ventricular chamber, the operator may use a catheter clip in accordance with various embodiments to secure the catheter in position. Specifically, the peelable cover on the base member may be removed, exposing the adhesive element, and the base member of the catheter clip may then be coupled to a convenient substrate, such as a drape, near the entry point into the radial artery. The catheter may then be placed within the catheter clip, and the catheter clip may be closed about the catheter, thereby securing the catheter with the inner gripping membrane. A procedure may then be performed via the catheter, the catheter clip permitting any small rotational and/or longitudinal adjustments to the catheter by the operator with the application of a small force, all without moving or opening the catheter clip. Once the procedure is complete, the catheter clip may be opened to release the catheter, which may then be withdrawn from the patient's body.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A clip for stabilizing a catheter, comprising:
   a frame member comprising:
      a first frame member portion;
      a second frame member portion hingeably coupled to the first frame member portion, the first and second frame member portions defining a first aperture therebetween; and
      a base member extending from the second frame member, the first and second frame members and base member being formed from a rigid or semi-rigid material; and
   an elastomeric inner gripping member extending inwardly from the frame member, comprising:
      a first elastomeric inner gripping member portion coupled to the first frame member portion, the first elastomeric inner gripping member portion comprising a first elastomeric membrane element and a first elastomeric reinforcing element; and
      a second elastomeric inner gripping member portion coupled to the second frame member portion, the second elastomeric inner gripping member portion comprising a second elastomeric membrane element and a second elastomeric reinforcing element;
      wherein the first and second elastomeric inner gripping member portions define a second aperture within the first aperture.

2. The clip of claim 1, wherein the base member is adapted to selectably couple the clip to a substrate.

3. The clip of claim 2, wherein the base member comprises an adhesive patch.

4. The clip of claim 1, wherein the second aperture is sized to receive a vascular catheter.

5. The clip of claim 1, wherein the first and second elastomeric reinforcing elements provide sufficient gripping force to prevent rotational and longitudinal motion of a catheter gripped within the second aperture, and wherein the first and second elastomeric membrane elements provide sufficient elasticity to prevent crimping of the catheter.

6. The clip of claim 4, wherein the first and second elastomeric reinforcing elements form a reinforcing ring when the clip is in a closed position.

7. The clip of claim 6, wherein the first and second elastomeric reinforcing elements each comprise a plurality of reinforcing ribs.

8. The clip of claim 4, wherein the first and second elastomeric membrane elements comprise an elastomeric material.

9. The clip of claim 8, wherein the elastomeric material comprises rubber, latex, or silicone.

10. The clip of claim 1, wherein the first and second elastomeric membrane portions provide sufficient elasticity to prevent crimping of a catheter gripped within the second aperture.

11. The clip of claim 10, wherein the frame member comprises a living hinge.

12. The clip of claim 10, wherein the first frame member portion, hinge portion, and second frame member portion comprise a unitary structure.

13. The clip of claim 1, wherein the frame member comprises plastic, polyethylene, or polypropylene.

14. The clip of claim 1, wherein the frame member comprises a closure member adapted to selectably retain the clip in a closed position.

15. The clip of claim 14, wherein the closure member comprises a pair of interlocking hook members.

16. The clip of claim 14, wherein the closure member comprises a thumb tab configured to facilitate opening of the clip.

17. The clip of claim 1, wherein the elastomeric inner gripping membrane is coupled to the frame member with adhesive.

18. The clip of claim 1, wherein the elastomeric inner gripping member is coupled to the frame via a tongue and groove interface.

19. The clip of claim 1, wherein the frame member comprises plastic, polyethylene, or polypropylene, and wherein the inner gripping member comprises rubber, latex, or silicone.

20. A method of using the clip of claim 1, the method comprising:
   inserting a catheter into the vasculature of a subject;
   advancing the adjustable catheter within the vasculature past a tortuosity; and
   securing the base of the clip to a substrate adjacent a portion of the catheter external to the body of the subject; and
   closing the clip about the catheter with the catheter passing through the second aperture of the clip.

* * * * *